United States Patent [19]

Lawson, Jr.

[11] 4,146,885
[45] Mar. 27, 1979

[54] INFANT BED AND APNEA ALARM

[76] Inventor: William H. Lawson, Jr., 4715 Webb Canyon Rd., Claremont, Calif. 91711

[21] Appl. No.: 841,808

[22] Filed: Oct. 13, 1977

[51] Int. Cl.$^2$ ............................................. G08B 21/00
[52] U.S. Cl. .................................... 340/573; 5/93 R; 5/108; 5/365; 128/2 R; 340/608
[58] Field of Search ............. 340/240, 279, 272, 608, 340/573; 128/2 R, 2 S, 1 B, 2.05 P; 5/93 R, 108, 365

[56] References Cited

U.S. PATENT DOCUMENTS

| | | | |
|---|---|---|---|
| 2,776,658 | 1/1957 | Gibbon | 5/108 X |
| 2,808,580 | 10/1957 | Fuller | 340/239 R |
| 3,631,438 | 12/1971 | Lewin | 340/240 |
| 3,727,606 | 4/1973 | Sielaff | 340/279 X |
| 3,993,042 | 11/1976 | Gatts | 128/1 B |

FOREIGN PATENT DOCUMENTS 1037383  7/1966  United Kingdom ..................... 340/279

Primary Examiner—John W. Caldwell, Sr.
Assistant Examiner—Daniel Myer
Attorney, Agent, or Firm—Lawrence Fleming

[57] ABSTRACT

A hospital bed or mattress for neonatal infants with a respiration monitor and alarm to detect apnea. No sensor or other appliance is attached to the infant. The bed comprises a base or frame structure with a soft resilient membranous top or cover, e.g., of sheet rubber. The closed air space below the pan is vented to the outside as by a small hole or tube, the average air pressure inside being about atmospheric. The baby's breathing causes slight rhythmic displacements of portions of the body, which in turn transmit small dynamic "recoil" forces proportional to acceleration to the flexible membrane on which the baby rests. The resulting diaphragm-like displacements modulate the air pressure inside. Breathing is sensed by monitoring this acoustic signal by a vented pressure microphone or by sensitive anemometer means connected to the vent. Acoustic and electrical filtering are used to discriminate against higher-frequency signals from the heart-beat and from ambient vibration. Cessation of the respiration signal for a predetermined period of time actuates an alarm.

10 Claims, 10 Drawing Figures

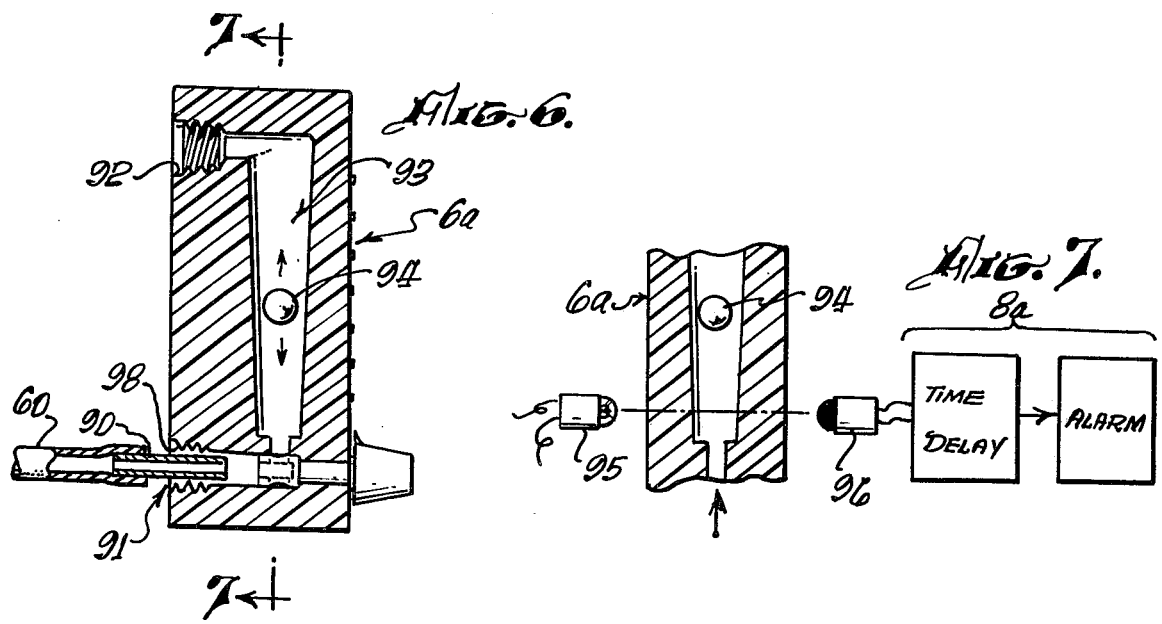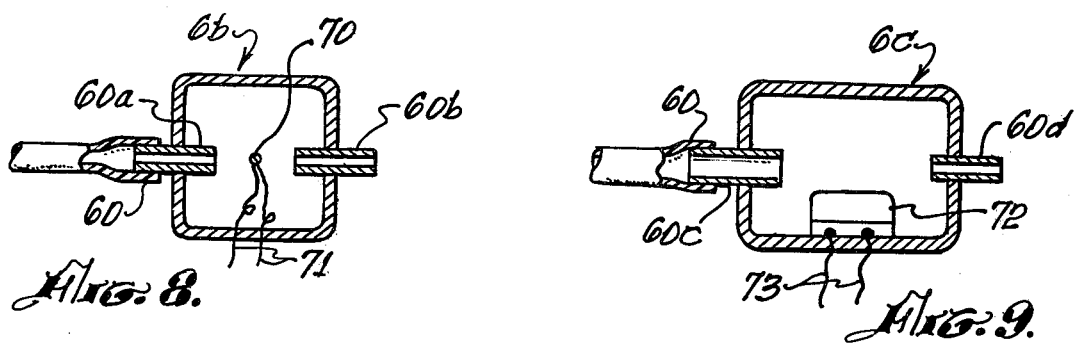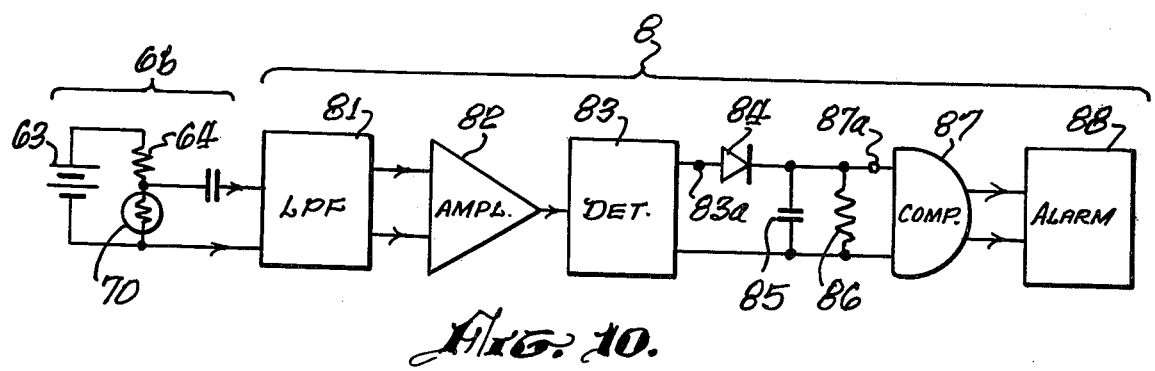

INFANT BED AND APNEA ALARM

BACKGROUND AND PRIOR ART

Apnea is a condition occurring in some newborn infants in which breathing ceases unexpectedly, as though the baby had forgotten to breathe. If apnea is detected in time, breathing can normally be restored by suitable stimuli. In hospital nurseries it is desirable to have automatic apnea alarm devices.

Some prior alarm devices of this class sense respiration by means of electrodes on the baby's skin, or sensors taped on the nose to sense air flow. Ferris, U.S. Pat. No. 3,325,799, shows a mattress equipped with resistance strain gages; U.S. Pat. No. 3,631,438 to Lewin shows a compartmented air mattress with thermistor anemometer means to sense differential air flow between compartments.

Electrodes or other elements attached to the skin are uncomfortable and subject to being dislodged. Special mattresses may be difficult to clean. Pressurized air mattresses may leak air. The functioning of special instrumented mattresses or pads as respiration sensors is affected by the resilience of the underlying surface.

It is desirable to provide an instrumented apnea-detecting infant bed as a complete structure with a substantially stiff base portion, without wiring or the like to the infant, not dependent on the retention of internal air pressure, and with a top removable for cleaning and sterilization.

BRIEF SUMMARY

This invention comprises a bed or mattress for neonatal infants, made in the form of a strong elastic membranous top of sheet rubber or the like fitted over a suitable frame. The frame may fit in a hosphital bassinet, fitting the inner walls snugly to provide a degree of sealing. The baby's weight is borne by the tensile resilience of the mattress top. The enclosed space below the pan is not pressurized, but is slow-vented to the atmosphere. The top and frame assembly is preferably removable for cleaning and sterilization.

Respiration is monitored by sensing the small dynamic variations in air pressure inside the pan induced by resilient diaphragm-like deflection of the top. A preferred sensing means is a sensitive anemomenter in the form of a self-heated thermistor posiitioned in the vent system. A pressure-sensitive microphone may alternatively be employed, or a variable-area flowmeter.

The rhythmic displacement of tissue in the chest region incident to breathing produces a small rhythmic recoil force against the surface on which the infant rests. The instantaneous orce is proportional to the instantaneous acceleration. The flexible membranous top of the bed translates this force into a diaphragm-like displacement, which in turn causes a corresponding dynamic fluctuation in the air pressure inside the base or pan.

A small hole or tube is provided to vent the air to the outside, with a time constant substantially longer than the period of a respiration cycle. The above pressure fluctuations cause a small dynamic air flow in and out of the vent. This flow is sensed by the anemometer means. The anemometer, or the flowmeter, thermistor or alternatively of the hot-wire type, provides an electrical signal analogous to the pressure fluctuations. This respiration signal is filtered and amplified by suitable known means, then detected and processed suitably to cause the actuation of a suitable alarm when the signal has ceased for a predetermined period of time. A suitable period is 5 or 10 seconds.

Since the dynamic pressure signal in the base is proportional to acceleration, it would be proportional — other parameters being assumed equal — to the square of the respiration rate. Other mechanical disturbances, such as the heart beat and ambient shock and vibration, are generally of higher frequency than the respiration rate. The frequency response of the system is preferably made "flat" for respiration, and other disturbances discriminated against, by suitable low-pass filtering in the electrical circuitry, plus acoustic filtering ahead of the sensing device.

Acoustic low-pass filtering may be provided in the air flow system ahead of the thermistor or other sensor, between the interior of the base and the sensor. A small-diameter tube or pipe may conduct the air to the sensor. The tube acts as an acoustic resistance, and the volume of air inside the base as an acoustic capacitance, providing the equivalent of an R-C low-pass filter. An additional enclosed chamber inside the base may be added to provide a two-section filter.

Because of static sag considerations, the natural frequency of vibration of the membranous top with a 3 or 4 kg infant resting on it is made preferably between about 2 and 6 Hz (120 to 360 cycles per minute), which is considerably higher than the average respiration rate. This frequency range may preferably be filtered out in the electrical circuitry.

The mattress may take the form of a rubber or like sheet with a rectangular wire frame molded into its periphery, made to fit about half-way down inside a known type of hospital bassinet or the like, with suitable supports for the frame. Another form of the invention comprises a similar rubber or like sheet fastened by suitable means over the open top of a rectangular or elliptical metal or plastic pan, providing a complete bed. The former construction is preferred.

DETAILED DESCRIPTION

FIG. 6 is a side sectional view of a flowmeter anemometer;

FIG. 7 is a section on line 7—7 of FIG. 6;

FIG. 8 is a section of a thermistor anemometer;

FIG. 9 is a section of a microphone anemometer; and

FIG. 10 is a block diagram of an amplifier and alarm circuit.

Figure 1:
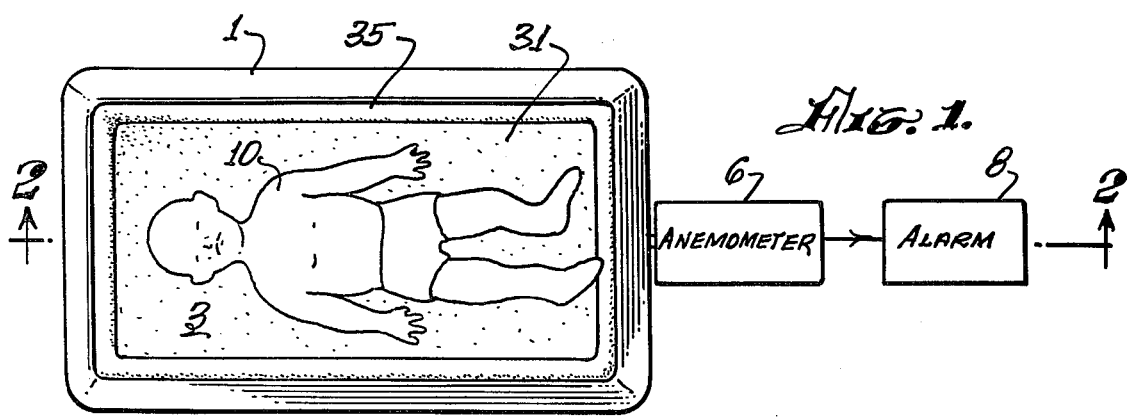
FIG. 1 is a top view of an infant mattress of the invention in place in a bassinet, with alarm means shown in block form.

FIG. 1 shows a baby 10 resting on a mattress 3 of the invention which is fitted into a hospital bassinet or similar pan-like structure 1. As shown better in FIG. 2, the preferred form of mattress comprises an impervious elastomeric membranous top 31 of sheet rubber or the like with stiffened edge portions 35 which fit generally snugly inside the walls of the bassinet 1. The edge portions 35 may be supported all around by suitable supports, such as angles 34. The space below the mattress top 31 is enclosed by the closed bassinet structure, except for an air vent tube 60. This vent communicates with the open air, as is shown later in FIGS. 6–9, so that the space under the mattress top 31 is not under any static pressure. The weight of the baby is supported entirely by the elastic resilience of the top 31.

As will be described in more detail later, the breathing of the baby 10 causes a slight rhythmic displacement of the mattress top 31, which in turn causes a corresponding rhythmic change in the enclosed volume of space 39 below it. The resulting dynamic variations in air pressure produce a small dynamic flow of air in and out the vent tube 60. This air flow is detected by suitable sensitive anemometer means 6. Absence of such air flow for a predetermined time actuates an alarm device 8. Specific anemometer and alarm means are described later in connection with FIGS. 6–10.

Figure 2:
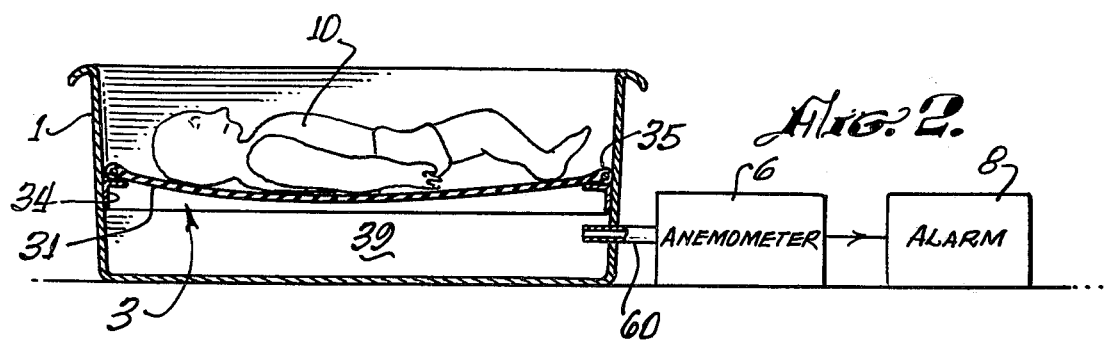
FIG. 2 is a side sectional view on line 2—2 of FIG. 1.
Figure 3:
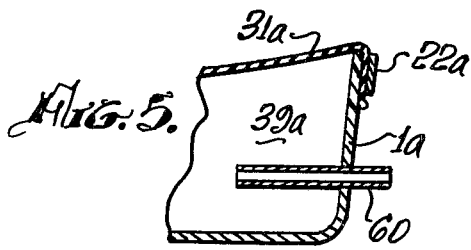
FIG. 3 is a cutaway partial perspective view of a frame-type mattress.
Figure 4:
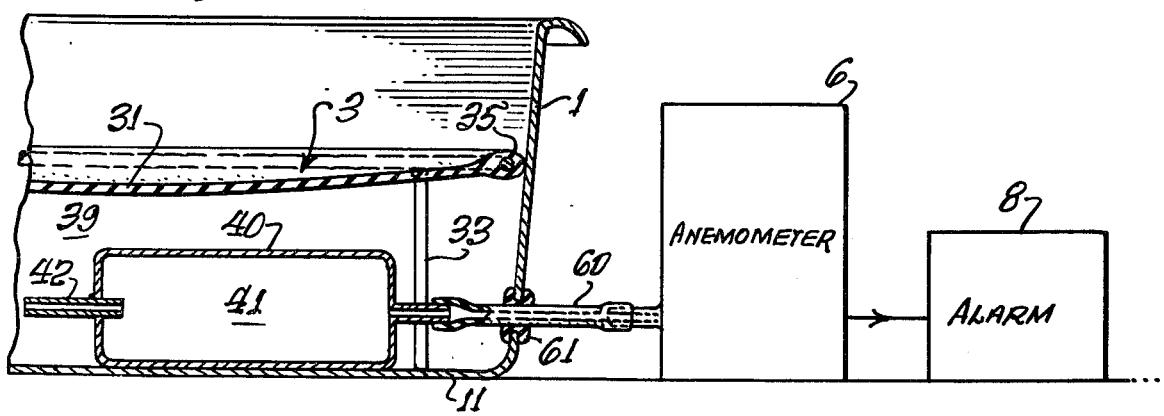
FIG. 4 is a partial side sectional view of a frame mattress in a bassinet, with acoustic filtering means.

FIG. 3 shows the construction of the mattress in more detail. The top 31, shown partly cut away, is molded or cast around a stiff wire frame or the like 32, the edge portions 35 being thick enough to provide substantially a resilient seal against the bassinet walls, as in FIG. 2. An alternative support means 33 is shown in FIG. 3, which may be used instead of the angle supports 34 of FIG. 2. These are legs which may stand on the bottom 11 of the bassinet 1 (FIG. 4). The legs 33 may be lengths of wire similar to the wire 32 and welded thereto. A typical such bassinet is about 40 cm. wide and 80 cm. long.

Figure 5:
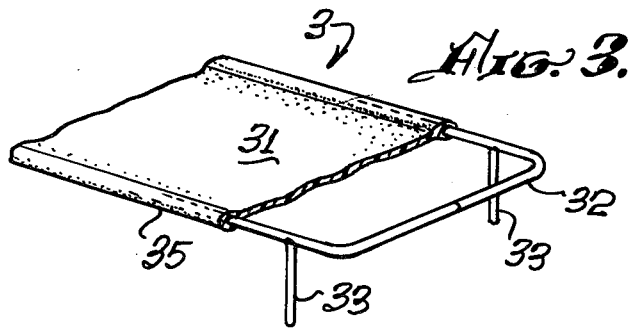
FIG. 5 is a partial sectional view of a modification.

FIG. 5 shows in section view a portion of a modification of the mattress of the invention. Here, a pan-like base 1a supports a sheet rubber or other elastomeric top 31a, on which the baby may lie in the same manner as in FIGS. 1 and 2. The top 31a is fastened to the open rim of base 1a by a suitable band or clamp means 22a, as shown. If a band is used at 22a, the base 1a may be circular or elliptical in plan or top view so that the band exerts a substantially even clamping force all around the circumference, in the manner of a hose clamp. Other known means of attaching the top 31a to the rim of base 1a may obviously be employed. This modification has the advantage of being manufacturable from commercially-available stock materials, i.e., sheet rubber and drawn metal pans, with a minimum of special tooling. It lacks, however, the high sides of a bassinet as in FIGS. 1 and 2, and so is less safe. An external wall-like structure, like the sides of a baby crib, could obviously be placed around the FIG. 5 modification to provide safety.

The space 39 under the top 31 in FIG. 2, and the corresponding space 39a in FIG. 5, are substantially sealed except for the vents 60. They do not have to be tightly sealed around the edges of top 31 or 31a, because the volume of space 39 or 39a is substantial compared to the air flow in and out of the vent 60. Any stray air leakage should, in practice, not be large in comparison to the flow through vent 60. A small puncture in top 31 or 31a does not, in general, affect substantially the monitoring of breathing by the anemometer devices 6. A force deflecting top 31 inward will increase the air pressure in space 39. Any leakage, plus that through vent 60, should be low enough so that such a pressure step persists for a time substantially longer than a respiration cycle, e.g., several seconds.

In FIG. 5, the top 31a is removable for cleaning or replacement. In the form of FIGS. 1–4, the whole mattress 3 may be lifted out of the bassinet 1 for cleaning or replacement.

The rim portion of base or pan 1a, FIG. 5, constitutes a substantially rigid frame-like member which supports and stiffens the circumference of the top 31a in the same manner as the supporting and stiffening frame 32 of FIG. 3.

The operation of the apnea monitoring system will now be described. The respiration of the infant 13 is preferably sensed by sensitive anemometer means responsive to the slight dynamic air flow in and out of the vent 60, FIGS. 2–5, 6, 8, 9, caused by the slight deflections of the top 31 incident to breathing. A preferred kind of sensor is a small self-heated thermistor 71 mounted inside a suitable sensor housing as 6B, FIG. 8. As is known, a minute air velocity will cool such a thermistor enough to cause a readily-measurable change in its resistance. Alternatively, a hot-wire anemometer of known design (not shown) may replace the thermistor 71. Either sensing element is preferably positioned directly in the vent air stream, as between the end of an inner vent tube 8 and an outer vent 9, as shown. Another alternative is a pressure microphone, to be described later in connection with FIG. 9. Another is a flowmeter, FIG. 6.

The small dynamic force on top 31 or 31a due to respiration is a recoil force due to the rhythmic shifting of the position of tissue and bone in the baby's chest region incident to breathing (since the mass of inspired air is balanced out by the increase in buoyancy in air). This dynamic force is proportional to the instantaneous acceleration of the tissue in motion. Hence, if it be assumed that the depth of respiration is constant while the rate may vary, the recoil force would be proportional to the square of the respiration rate. However, rapid respiration is normally shallower, so that the force/rate relation is less than a square-law function.

It is desirable, however, to provide means to further discriminate against higher-frequency artifacts due to heart beat and to "bouncing" of the baby on the bed due to excitation of its lowest natural frequency by ambient vibration and shock in the building. It is not convenient to place the lowest natural frequency at or below the normal respiration rate, because the static sag would be excessive.

As is known, in a simple linear mass-spring oscillating system, the static sag $y_s$ of the mass on the spring in the earth's gravitational field is expressed by $$y_s = g/\omega^2 = 24.5/f^2$$

where $y_s$ is the static sag in centimeters, $\omega = 2\pi f$, and $f$ is the natural frequency of oscillation in Hz. For a natural frequency of 1 Hz, $y_s$ would be 24.5 cm., which is impracticably large. A convenient value for $y_s$ at the center portion of the bed may be about 2 cm. due to the baby's weight. To a first approximation this yields a lowest natural frequency of 3.3 Hz, or about 210 cycles per minute, which is far above the respiration rate, which, for a newborn baby, may typically be about 40 per minute. This relatively high frequency may be filtered out of the alarm system by both acoustic and electrical filters designed in known manner.

In FIG. 2, relatively high-frequency oscillations in air pressure in the interior space 52 may be attenuated more than slower oscillations by providing a flow-restricting orifice (vent) or the small-bore tube 60 at the exit from space 39 to act as an acoustic resistance. The space or chamber 39 and resistance act as a single-section R-C low-pass acoustical filter, the enclosed space 39 being the acoustical capacitance. The attenuation rate is 6 db per octave, i.e., the output is inversely proportional to the first power of the frequency.

A second acoustic filter section may be added, FIG. 4, to double the attenuation rate, the output (dynamic air velocity through tube 60) then being inversely proportional to the square of the frequency. In FIG. 4, the internal space 39 is coupled into a second space or chamber 41 via another acoustic resistance, such as a small-bore tube 42. The chamber (acoustic capacitance) 41 may be made by suitably enclosing a portion of the space 39 by a wall or box 40. The design of acoustic filters is described for example in the book, "Dynamical Analogies" by Harry F. Olson, published by Van Nostrand, New York, 1943.

The dynamic pressure variations of the air from vent or tube 60, which constitutes the respiration signal to be sensed, may be sensed by a sensitive variable-area flowmeter, FIGS. 6–7, by a thermistor, FIG. 8, or by a vented pressure microphone, FIG. 9.

Referring first to FIGS. 6 and 7, the air from vent 60 is applied to the inlet of a variable-area flowmeter 6a. Such known instruments are also known as "rotameters". Air or other fluid moving upward in the diverging bore 93 causes a ball 94 to rise therein. Its upward displacement is generally about proportional to the flow rate in the inlet 98, up the bore 94, and out the outlet 92. FIG. 6 is a section of a small commercial unit of this type which has a narrowly-diverging bore, and a pith ball at 94. The vent tube 60 is not sealed to the inlet 98, but "blows" into it with a clearance 91 between the tube 90 and the inlet opening 98. The flow rate in the meter bore 93 is then a function of the velocity of the air in tube 90. The main reason for the clearance 91 is to permit air to be sucked into tube 90, as well as to blow out; without such provision, a decrease in air pressure in space 39 or 41 would be blocked, the ball 94 sealing the bore inlet at the bottom.

In use, the pith ball 94 tends to "float" a few cm up in the bore 93 in response to a small "a-c" or dynamic air flow in and out of tube 90. This is due to the very small mass/area ratio of the ball, which is slowed by the viscosity of the air, and also to a degree of acoustic rectifying action adjacent the mouth of tube 90. Such rectification is a subject little-explored; it was used in a valveless air pump described by T. M. Dauphinee of the National Research Council of Canada. The momentum of air coming out of tube 90 tends to move it straight ahead and into the bore 93, instead of reversing direction and flowing out through the clearance 91. Air drawn into tube 90, however, will more readily pass into the annular clearance 91 and reverse direction into the tube mouth, because of its lower velocity. Thus, there is a tendency for an "a-c" dynamic pressure in space 39 to produce a slight net "d-c" or steady upward component of air flow in the meter bore 93. A related phenomenon is employed in the well-known cup anemometer, whose direction of rotation is independent of the direction of the wind. The requirement for such a rectification effect is a directional bias in impedance or resistance to air flow at some predetermined point in an air stream.

It is considered impractical to try to provide flap valves or the like in a system with extremely low rates of air flow, in this case of the order of 0.1 to 1 cc per second, and at very low pressures. Hence, the valveless rectifying action just described appears to offer the only way to derive the desirable d-c or steady component of flow from a purely "a-c" or alternating flow, such as is found at the tube 60.

The position of the flowmeter ball 94 is preferably sensed by photoelectric means, shown in FIG. 7. The body of the meter 6a is transparent or provided with suitable windows. A light source 95 and a photoelectric detector, such as a photo-transistor, are positioned opposite each other so that the light beam is interrupted when the meter ball 94 falls to a predetermined height near the bottom. Photodetector 96 is connected to suitable amplifying and time delay means which in turn actuate an alarm device, all indicated at 8a. The circuitry, of any suitable known design, is arranged to actuate the alarm after the light beam has remained interrupted for a predetermined time, typically 5 to 10 seconds. The time is made adjustable. This form of the invention has the advantage of providing a visual signal of breathing, even if the electrical system or the electric power fails.

FIGS. 8 and 9 show alternative means of sensing slight air flow in and out of tube 60. In FIG. 8, a small bead-type thermistor 70 is positioned in the air stream inside a suitable box or compartment 6b. The thermistor 70 is self-heated electrically, as by a power source 63 and series resistor 64, FIG. 10. Air flowing over the bead cools it, changing its resistance, and hence the voltage across it. Such detectors are highly sensitive. An example of such use is shown in U.S. Pat. No. 3,631,438 to J. F. Lewin. In FIG. 8, the inlet tube 60 and the exit vent tube 60b preferably have about the same bore diameter, so that the air velocity over the thermistor 70 will be about the same in either direction.

In the modification of FIG. 9, a pressure microphone 72 is employed as the sensor. It is mounted inside a small chamber or housing 6c which may be similar to the housing 6b of FIG. 8. Acoustic pressure comes into chamber 6c via the tube or the like 60, as before. However, the exit vent 60d to the outside atmosphere is substantially smaller, i.e., more flow-restrictive, than the vent 60b of FIG. 8, to permit retention in chamber 6c of dynamic pressure in the frequency range of interest. Release of a pressure step in space 39 through vent or tube 60d may suitably have a time constant of several seconds. Such vented pressure microphones have been used for sensing infrasonic sound in the atmosphere, such as are caused by far-distant storms and explosions.

It may be noted that in the forms of the invention of FIGS. 8 and 9, the sensing elements 70 or 72 deliver output signals proportional to the dynamic pressure in the space 52 in the frequency range where tube or vent 60 acts primarily as an acoustic resistance, because then the rate of flow through vent tube 60 is proportional to the pressure applied.

A suitable set of electronic circuitry to process the signal output of a thermistor 70 (FIG. 8) is shown in block form in FIG. 10, and may be designed in known manner. Heating current is applied to thermistor 70 from a voltage source 63 through a suitable impedance 64. Voltage variations across thermistor 70, due to its heating and cooling, are fed through a suitable low-pass filter 81, a suitable amplifier 82, and an amplitude detector 83, which in turn delivers a d-c output voltage at point 83a proportional to the amplitude of the dynamic changes in voltage across thermistor 70. This output signal voltage maintains a charge on a capacitor 85 via a diode 84. If the output of detector 83 drops to zero or a relatively low value, i.e., if apnea occurs, the voltage across capacitor 85 will drop slowly as the capacitor discharges through a suitable resistor 86. The R-C time constant may typically be 5 to 10 seconds.

A comparator circuit 87 is connected so as to produce an output signal when the d-c signal voltage at terminal 87a drops to a value at or near the potential of terminal 83a. The comparator output operates to energize an alarm device 88. The alarm device 88 may be an audible or visual alarm of any suitable known type.

In the claims, the term "substantially closed space" means a space 39 or 39a, FIGS. 1-4, which is enclosed except for vent 60 and minor leaks.

The term "acoustic capacitance" means a chamber or space enclosed except for communicating tubes or vents. In analogy to electrical capacitance, the acoustic capacitance of such a space is taken as generally proportional to its volume. The term "acoustic resistance" means a tube, passage, or the like, wherein the air flow in volume per unit time is proportional to the pressure difference between its ends. In analogy to electrical resistance, a high acoustic resistance permits but a small flow at a given pressure, as in a long small-diameter tube.

I claim:

1. An infant bed and apnea alarm comprising:
   a substantially flat bed top of soft impervious sheet-like elastomeric material having a perimeter portion;
   a substantially rigid frame-like member secured thereto all around said perimeter and stiffening it;
   an open-top pan-like enclosure closely surrounding said perimeter and defining a substantially empty and enclosed air space below said top, and
   means supporting said top removably to said enclosure,
   said top being adapted to support an infant by its diaphragm-like mechanical tension without pressurization thereunder;
   vent means including an exit vent and permitting moderate air flow between said air space and the atmosphere, and
   respiration sensing means sensing air velocity in said vent means.

2. The structure of claim 1 wherein:
   said frame-like member is a wire frame bonded to said top around its said perimeter,
   and said enclosure is a pan-like bassinet having a closed bottom,
   said top fitting inside said bassinet generally in a plane between its rim portion and bottom, and said perimeter fitting closely the walls of said bassinet.

3. The structure of claim 2, further comprising:
   ledge-like support means in said bassinet engaging said perimeter substantially in said plane.

4. The structure of claim 2, further comprising:
   leg members attached to said frame-like member and extending downward to said bottom of said bassinet to support said top in said plane.

5. The structure of claim 1, wherein:
   said frame-like member is the open top rim portion of said pan-like enclosure,
   said perimeter portion engaging said rim portion all around and being removably retained thereon.

6. The structure of claim 1, wherein:
   said respiration sensing means comprises an anemometer means connected by a first passage to said space to sense cyclic dynamic air movement through said passage and produce an anemometer output signal at output terminals in response thereto;
   signal time delay means in actuable connection to said terminals, and
   an alarm device actuated by said time delay means,
   and wherein said perimeter portion has substantial thickness to provide substantially a resilient seal to said enclosure.

7. The structure of claim 6, wherein:
   said first passage has the property of an acoustic resistance and said space has a substantial acoustic capacitance, said resistance and capacitance being of magnitudes to form a single-section low-pass filter operable in the frequency range between about 20 and 100 cycles per minute.

8. The structure of claim 7, further comprising:
   a second acoustic low-pass filter section comprising a chamber and a second passage and connected between said space and said first passage.

9. The structure of claim 6, wherein:
   said anemometer means comprises a variable-area flowmeter having a diverging bore and a light ball adapted to rise therein in response to air flow into an inlet, and further comprising:
   an air tube from said vent means into said inlet with a clearance around said tube forming a portion of said exit vent; and
   photoelectric cell means to sense the height of said ball and adapted to generate said anemometer output signal.

10. The structure of claim 6, wherein:
    said anemometer means comprises a thermistor enclosure,
    a thermistor mounted therein,
    tube means directing air in said vent means onto said thermistor,
    exit tube means communicating with the atmosphere and directing inspired air onto said thermistor, and
    a current supply to self-heat said thermistor.

* * * * *